United States Patent [19]

Maeda et al.

[11] Patent Number: 4,990,459
[45] Date of Patent: Feb. 5, 1991

[54] IMPURITY MEASURING METHOD

[75] Inventors: Ayako Maeda, Kawasaki; Mokuji Kageyama, Yokohama; Shintaro Yoshii, Tokyo; Masanobu Ogino, Yokosuka, all of Japan

[73] Assignee: Kabushiki Kaisha Toshiba, Kawasaki, Japan

[21] Appl. No.: 339,825

[22] Filed: Apr. 18, 1989

[30] Foreign Application Priority Data

Apr. 25, 1988 [JP] Japan .................................. 63-102199

[51] Int. Cl.$^5$ .............................................. G01N 1/00
[52] U.S. Cl. .................................... 436/178; 436/174; 436/177
[58] Field of Search ............... 436/178, 174, 150, 151, 436/149, 5, 177; 422/98, 68

[56] References Cited

U.S. PATENT DOCUMENTS

| | | | |
|---|---|---|---|
| 3,490,873 | 1/1970 | Corl | 436/5 |
| 3,830,094 | 8/1974 | Leger | 73/15.4 |
| 3,958,940 | 5/1976 | Conway | 23/230 L |
| 4,007,010 | 2/1977 | Woodbridge, III | 422/61 |
| 4,584,886 | 4/1986 | Matsunaga et al. | 73/863 |
| 4,634,497 | 1/1987 | Shimazaki | 156/646 |

OTHER PUBLICATIONS

Juan Ramirez-Munoz, "General Principles and Characteristics," Atomic Absorption Spectroscopy and Analysis by Atomic-Absorption Flame Photometry, Chapter 2, Elsevier Publishing Company, pp. 11-14, 1968.

Primary Examiner—Robert J. Hill, Jr.
Attorney, Agent, or Firm—Finnegan, Henderson, Farabow, Garrett, and Dunner

[57] ABSTRACT

A drop which is hydrophobic to the surface of an object to be measured is dropped on the surface of the object and moved so as to be brought into contact with the overall surface of the object to be measured. After the movement, the drop is recovered and analyzed by chemical analysis to measure the kind of element and content of an impurity adsorbed on the surface of the object to be measured.

6 Claims, 5 Drawing Sheets

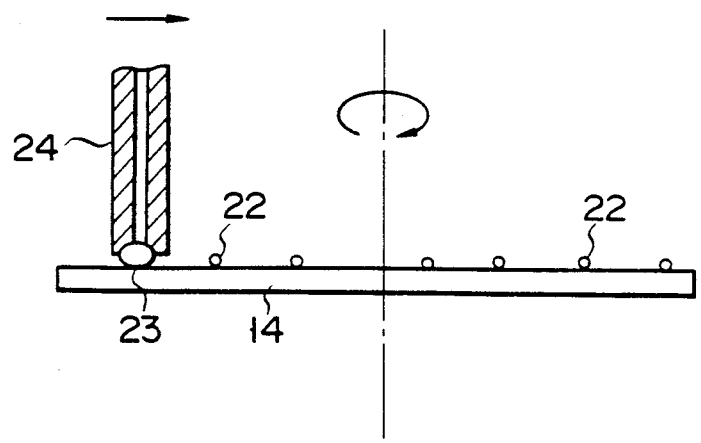
F I G. 8
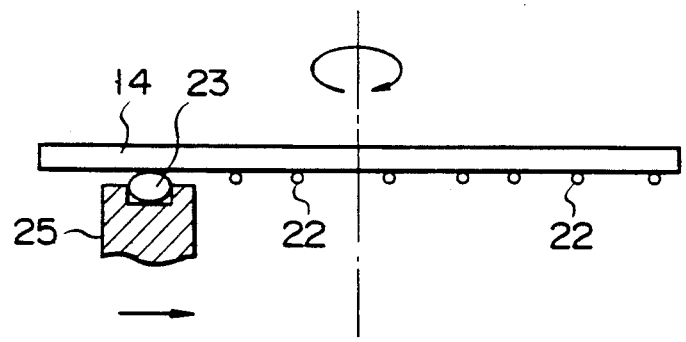
F I G. 9

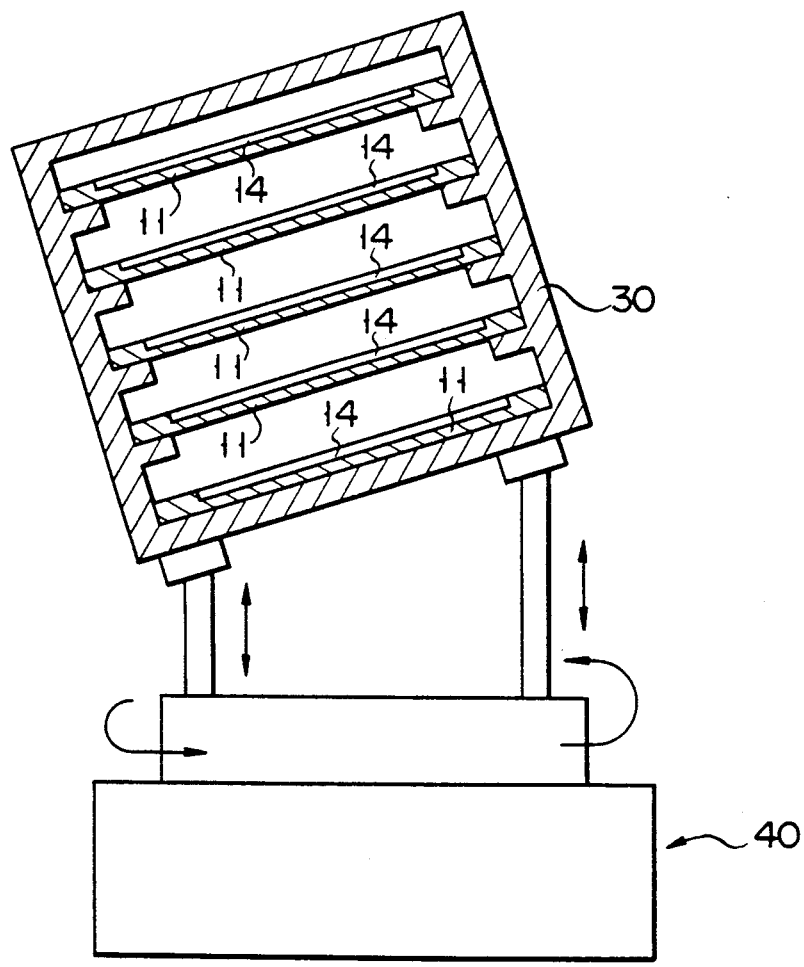
F I G. 10

IMPURITY MEASURING METHOD

Background of the Invention

1. Field of the Invention

The present invention relates to an impurity measuring method and apparatus for determining the type and content of an impurity adsorbed on the surface of an object to be measured, especially a semiconductor wafer.

2. Description of the Related Art

It is well known that when an impurity such as sodium (Na), potassium (K) or iron (Fe) is contained in a thin film of, e.g., an oxide film formed on a semiconductor wafer, electrical characteristics of a semiconductor device are significantly adversely affected even if the impurity is very small. Therefore, in order to improve the electrical characteristics of the semiconductor device, diffusion of the impurity from the wafer surface must be reduced as much as possible. For this purpose, a level of contamination on the wafer surface must be correctly analyzed and measured.

The level of contamination on the wafer surface is conventionally measured by using secondary ion mass spectrometry, Auger spectroscopic analysis or neutron activation analysis. Since these methods require a large-scale, expensive measuring instrument, an analysis cost is increased. In addition, a skill is required in an analyzing operation. Also, since each analyzing method uses an electron or light beam, local analysis can be performed, but the gross content of contamination on the overall surface cannot be estimated.

For this reason, in place of the above instrumental analyzing methods, a method of easily measuring the content of contamination on the overall surface of a substrate wafer was proposed. In this method, an oxide film of a predetermined thickness with an impurity included therein is formed beforehand on the surface of a substrate and dissolved by using a hydrofluoric acid vapor, and the resultant solution is recovered to measure an impurity by using a spectroscopic analyzer. This method is called vapor phase decomposition method. This method, however, requires an oxide film formation step. In this oxide film formation step one of the following occurs, an impurity is diffused from an oxidation atmosphere into an oxide film, the impurity evaporates from the wafer surface into the oxidation atmosphere, the impurity is diffused from the wafer surface into the substrate or the impurity contained in the substrate is diffused into the oxide film. This method is undesirable in terms of reliability in analysis values.

In another conventional method, without forming an oxide film on the surface of a substrate by an oxidation step, the overall substrate is dipped in a hydrofluoric acid solution to dissolve a native oxide film naturally formed on the substrate surface, and the resultant solution is recovered to measure an impurity content by using a spectroscopic analyzer. In this method, however, since an extremely large volume of the hydrofluoric acid solution is required for recovering the impurity by dipping a whole wafer, the concentration of the impurity contained in the solution is significantly decreased, and therefore analysis sensitivity and precision are degraded. In addition, according to this method, there is a very high probability that the hydrofluoric acid solution will be contaminated by impurities on or in the vessel itself.

Summary of the Invention

It is an object of the present invention to provide an impurity measuring method and apparatus which can measure the content of an impurity adsorbed on the surface of an object to be measured with high sensitivity and precision and which realizes a low analysis cost and high reliability.

(1) An impurity measuring method of the present invention comprises the steps of, in the case of a hydrophobic object, dropping a drop of a solution to the surface of an object to be measured, moving the drop dropped on the surface of the object to be measured so that the drop is kept in contact with the surface of the object to be measured, recovering the drop after the movement, and analyzing the recovered drop by chemical analysis to determine the type and content of an impurity adsorbed on the surface of the object to be measured.

(2) An impurity measuring method of the present invention comprises the steps of, in the case of a hydrophilic object, directing a vapor from a solution which is hydrophobic to the surface of the object to be measured onto that surface to render the surface hydrophobic, dropping a drop of a solution to the surface of an object to be measured, moving the drop dropped on the surface of the object to be measured so that the drop is kept in contact with the surface of the object to be measured, recovering the drop after the movement, and analyzing the recovered drop by chemical analysis to determine the type and content of an impurity adsorbed on the surface of the object to be measured.

(3) In addition, an impurity measuring method of the present invention comprises the steps of bringing a drop of a solution of an object to be measured into contact with the surface of the object to be measured and holding the drop thereon, and scanning the drop on the surface of the object to be measured by a combination of rotational and linear motions, recovering the drop after the scanning, and analyzing the drop by chemical analysis to determine the type and content of an impurity adsorbed on the surface of the object to be measured.

(4) Also, an impurity measuring apparatus of the present invention comprises a holding table for holding an object to be measured on which a drop of a solution for a surface treatment is to be dropped, an analyzing vessel for housing the holding table, and a driving mechanism for giving a motion to the analyzing vessel so that a drop dropped on the surface of the object to be measured is kept in contact with the surface of the object to be measured and moved throughout the overall surface thereof.

According to the measuring method of the present invention, a drop of a solution is dropped, and the solution drop is moved in contact with the surface of an object to be measured, thereby recovering into the drop an impurity present on the surface of the object to be measured into the drop.

The above mentioned drop is not brought into contact with anything but the surface of the object to be measured. Because the drop is sufficiently small in size, small amounts of impurities can be dissolved at a high enough concentration such that highly reliable measurements can be performed with sensitivity and precision.

According to the measuring apparatus of the present invention, the drive mechanism moves a solution dropped on the surface of an object to be measured so that the solution drop can be brought into contact with the overall surface of the object to be measured.

According to the present invention, there is provided an impurity measuring method and apparatus which can measure an impurity adsorbed on the surface of an object to be measured with high sensitivity and precision and which realizes a low measuring cost and high reliability.

Brief Description of the Drawings

FIGS. 7 to 9 are sectional views showing modifications of the method of the second embodiment; and FIG. 10 is a view showing an arrangement of an apparatus used in the present invention.

Detailed Description of the Preferred Embodiments

Embodiments of the present invention will be described in detail below with reference to the accompanying drawings.

Figure 1:
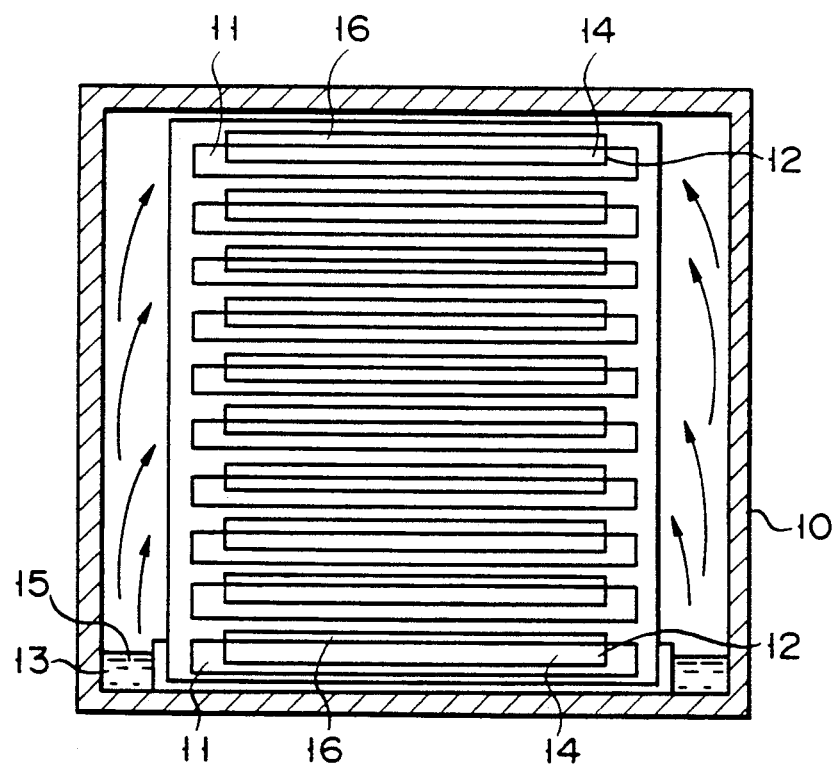
FIG. 1 is a front view showing an arrangement of a vessel used for carrying out a method according to a first embodiment of the present invention.

A closed vessel 10 having a structure as shown in a front view of FIG. 1 is prepared. A plurality of wafer holding tables 11 are set in the closed vessel 10 with predetermined vertical intervals therebetween. A recess portion 12 having the same shape as that of a semiconductor wafer is formed in each wafer holding table 11 to receive the wafer. A groove portion 13 is formed in a bottom portion of the vessel 10 to contain a solution.

After a silicon semiconductor wafer 14 is inserted as an object to be measured in the recess portion 12 of each wafer holding table 11, the table 11 is set at a predetermined position of the vessel 10, and a hydrofluoric acid (HF) solution 15 is filled as a solution in the groove portion 13 formed in the bottom portion. Note that a native oxide film 16 is formed on the surface of each wafer 14. Thereafter, the vessel 10 is closed by a cover (not shown) and kept at room temperature for about 30 minutes. As a result, the hydrofluoric acid solution 15 evaporates, and the closed vessel is filled with a vapor of the hydrofluoric acid. The native oxide film 16 formed on the surface of each wafer is brought into contact with and dissolved by the hydrofluoric acid vapor, and a small volume of the solution adsorbs on the wafer surface.

Figure 2:
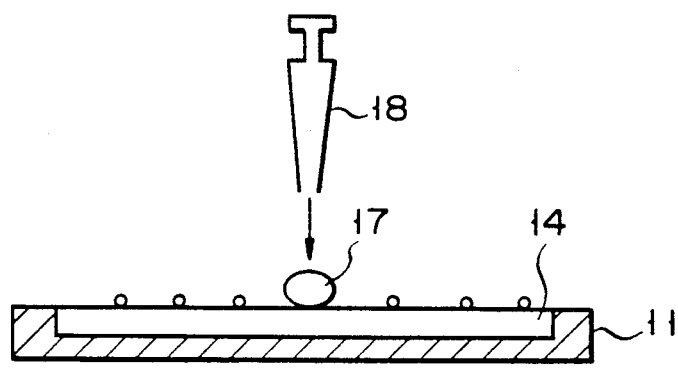
FIGS. 2 and 3A to 3C are sectional views for explaining the method of the first embodiment.

The wafer 14 treated as described above is extracted together with the wafer holding table 11 from the closed vessel 10. As shown in a sectional view of FIG. 2, a drop 17 (50 to 200 μl) of a hydrofluoric acid solution having a concentration of 0.5% to 2% is dropped on the surface of the wafer 14 by a micropipette. A high-purity hydrofluoric acid solution having an impurity concentration of 100 ppt or less was used as the solution drop 17. At this time, since the wafer 14 has become hydrophobic by the above treatment using the hydrofluoric acid vapor, the drop 17 does not wet the wafer surface, leaving a round droplet on the surface as shown in FIG. 2.

Figure 3A:
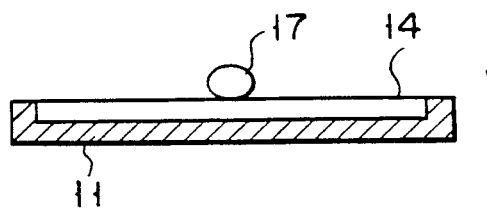
Figure 3B:
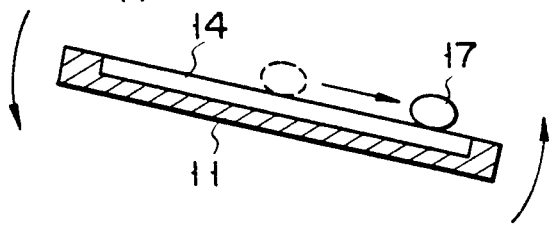
Figure 3C:
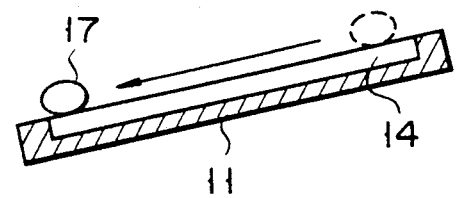
Figure 4:
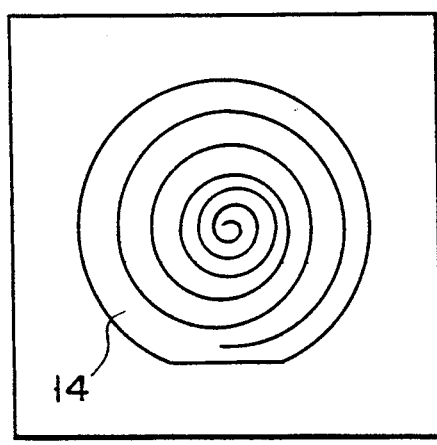
FIGS. 4 and 5 are views showing a locus of a solution drop in the method of the first embodiment, respectively.
Figure 5:
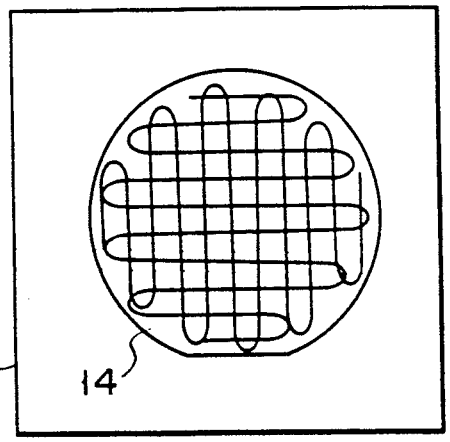

Thereafter, as shown in FIGS. 3A, 3B and 3C, the wafer 14 and the wafer holding table 11 are inclined or rotated in various directions to move the drop on the overall surface of the wafer so that a locus of the drop becomes spiral as shown in FIG. 4. Alternatively, the drop is moved on the overall surface of the wafer so that a locus of the drop continuously repeats U-turns as shown in FIG. 5. In this manner, the solution in which the native oxide film adsorbed on the wafer surface is dissolved is recovered by the drop of the hydrofluoric acid solution dropped on the wafer surface.

The drop in which the solution is recovered is then sampled by a pipette or the like and analyzed by chemical analysis using a spectroscopic analyzer, thereby determining a level of contamination of the wafer. Note that dissolution of the native oxide film on the wafer surface and dropping and moving of the hydrofluoric acid solution were performed by using a glove box having a 0.3-μm ULPA filter and a cleanness of class 10 or less.

According to the method of the above embodiment, measurement cost is decreased because no expensive measuring instrument is required. In addition, the volume of the hydrofluoric acid solution containing the native oxide film formed on the wafer surface can be decreased much more than that in the case wherein the wafer is dipped in the hydrofluoric acid solution. For example, in order to dip the wafer in the hydrofluoric acid solution to dissolve the native oxide film, about 5 ml of the hydrofluoric acid solution are required. In the method of the above embodiment, however, only about 100 μl of the solution are needed for dropping. For this reason, an impurity concentration in the solution becomes 50 times that in the conventional method. Furthermore, the recovered solution drop is not brought into contact with anything but the wafer surface, and only the native oxide film containing the impurity on the wafer surface is dissolved therein. Therefore, since the drop is sufficiently small in size that small amounts of impurities can be dissolved at high concentrations and no external impurity contamination occurs, highly reliable measurement can be performed with high sensitivity and precision. As a result, an impurity of about $10^9$ to $10^{10}$ (atoms/cm$^2$) on the wafer surface can be rapidly and easily measured without an oxidation step.

A second embodiment of the present invention is described below.

In the method according to the second embodiment, as in the method of the first embodiment, a native oxide film formed on the surface of a wafer is dissolved by a treatment using a vapor of a hydrofluoric acid solution.

Figure 6:
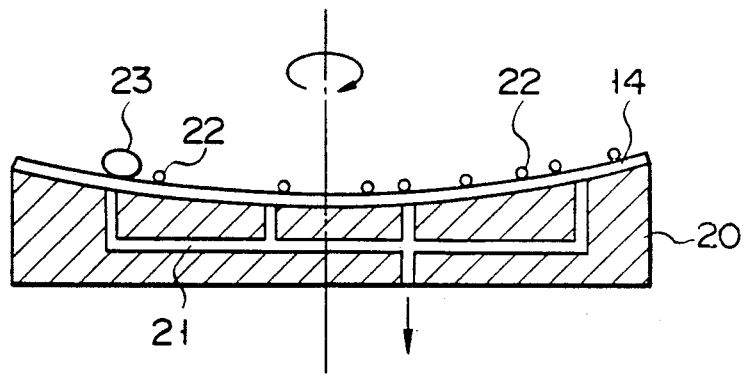
FIG. 6 is a sectional view showing a method according to a second embodiment of the present invention.

Thereafter, as shown in a sectional view of FIG. 6, a wafer 14 is brought into contact with a jig 20 having a recess portion. The wafer 14 is brought into contact with the jig 20 by evacuating the jig 20 through a tube 21 formed in the jig 20 and chucked from the back side surface of the wafer 14. In FIG. 6, solutions 22 in which a native oxide film is dissolved are adsorbed on the surface of the wafer 14.

A drop 23 (50 to 200 μl) of a hydrofluoric acid solution having a concentration of 0.5% to 2% is dropped by a micropipette or the like at an end portion of the surface of the wafer in contact with the jig 20. A high-purity hydrofluoric acid solution having an impurity concentration of 100 ppt or less was used as the solution drop 23. At this time, since the wafer 14 has become hydrophobic by the above treatment using the hydrofluoric acid vapor, the drop 23 does not wet the wafer surface, leaving a round droplet on the surface as shown in FIG. 6.

Thereafter, as shown in FIG. 6, the jig 20 is rotated about its center in a horizontal plane. The rotational speed is about 5 to 40 rpm. As a result, the drop 23 of the hydrofluoric acid solution dropped at the end portion of the wafer surface is moved by centrifugal force and gravity while it recovers the solutions 22 adsorbed on the wafer 14. In this manner, the solutions 22 adsorbed on the wafer surface are recovered.

Thereafter, as in the first embodiment, the drop 23 which recovered the solutions is sampled by a pipette or the like and analyzed by chemical analysis using a spectroscopic analyzer to determine the type and content of the impurity, thereby determining a level of contamination of the wafer.

Also in the method of the second embodiment, measurement cost is decreased because no expensive measuring instrument is required. In addition, since the solution drop has a small enough volume that small amounts of impurities can be dissolved at high concentrations and no external impurity contamination occurs, highly reliable measurement can be performed with high sensitivity and precision.

Figure 7:
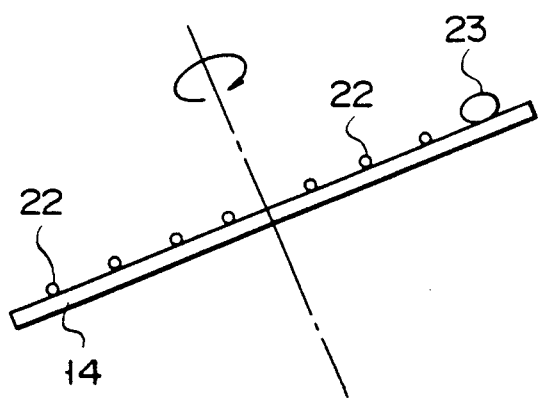

As a modification of the method of the second embodiment shown in FIG. 6, a wafer 14 may be rotated by inclining a rotational axis without using a jig having a recess portion, as shown in FIG. 7, thereby moving a drop 23 on a wafer surface. In the methods shown in FIGS. 6 and 7, when no pipette-like jig or the like is used, mixing of an impurity from such a jig can be prevented.

As another modification of the method of the second embodiment shown in FIG. 6, a drop 23 may be brought into contact with a wafer surface while it is supported by a pipette-like jig 24, as shown in a sectional view of FIG. 8. Thereafter, a wafer 14 is rotated and at the same time the drop 23 supported by the jig 24 is horizontally moved as shown in FIG. 8, thereby recovering solutions 22 adsorbed on the wafer surface.

As still another modification of the method of the second embodiment shown in FIG. 6, a wafer 14 may be supported so that its surface faces down so as to bring a drop 23 supported on a plate-like jig 25 into contact with the wafer surface, as shown in FIG. 9. Thereafter, the wafer 14 is rotated and at the same time the drop 23 supported by the jig 25 is horizontally moved as shown in FIG. 9, thereby recovering solutions 22 adsorbed on the wafer surface.

In the method wherein a drop is dropped on a wafer and then the wafer is moved to recover solutions on the wafer surface as shown in FIG. 3 or 7, an analyzing vessel 30 capable of housing a plurality of wafers 14 and a drive mechanism 40 for moving the vessel 30 may be used as shown in a sectional view of FIG. 10, thereby increasing the recovery efficiency. In such an apparatus, without using the analyzing vessel 30, a wafer holding table which houses one wafer may be moved by the drive mechanism 40 to recover solutions along the locus as described above.

Examples of the solutions that can be used are:
(1) HF
(2) $HF+HNO_3$
(3) $HF+H_2O_2$
(4) $HCl+H_2O_2$ The present invention is not limited to the above embodiments but can be variously modified. For example, in the above embodiments, the present invention is applied to measurement of an impurity on the surface of a semiconductor wafer. The present invention, however, can be applied to, e.g., measurement of an impurity in a silicon oxide or silicon nitride film, or general measurement of a level of contamination on the surface of a metal. In addition, the kind of a solution for dissolving a deposition layer on the surface of an object to be measured can be arbitrarily selected in accordance with the kind of object material. Furthermore, if the surface of an object to be measured is hydrophobic with respect to a drop to be dropped next, the step of rendering the surface hydrophobic by using a vapor of a solution need not be performed.

What is claimed:
1. An impurity measuring method comprising the steps of:
   dropping a drop of a solution to the surface of a hydrophobic object to be measured on the surface of said object to be measured;
   moving said drop dropped on the surface of said object to be measured so that said drop is kept in contact with the surface of said object to be measured;
   recovering said drop after the movement; and
   analyzing said recovered drop by chemical analysis to determine the type and content of an impurity absorbed on the surface of said object to be measured.

2. An impurity measuring method according to claim 1, in which as said solution use is made of one selected from the group consisting of HF, $HF+HNO_3$, $HF+H_2O_2$ and $HCl+H_2O_2$.

3. An impurity measuring method comprising the steps of:
   in the case of a hydrophilic object, rendering the surface of an object to be measured hydrophobic by using a vapor of a solution which is hydrophobic to the surface of said object to be measured;
   dropping a drop of a solution on the surface of said object to be measured;
   moving said drop dropped on the surface of said object to be measured so that said drop is kept in contact with the surface of said object to be measured;
   recovering said drop after the movement; and
   analyzing said recovered drop by chemical analysis to determine the type and content of an impurity adsorbed on the surface of said object to be measured.

4. An impurity measuring method according to claim 3, in which, in the case of a hydrophilic object, said vapor is HF and, as said solution used in the dropping step, use is made of one selected from the group consisting of HF, $HF+HNO_3$, $HF+H_2O_2$ and $HCl+H_2O_2$.

5. An impurity measuring method comprising the steps of:
   bringing a drop of a solution to the surface of a hydrophobic object to be measured into contact with the surface of said object to be measured and holding said drop thereon, and moving said drop on the surface of said object to be measured by a combination of rotational and linear motions;
   recovering said drop after the movement; and analyzing said drop by chemical analysis to determined the type and content of an impurity adsorbed on the surface of said object to be measured.

6. An impurity measuring method comprising the steps of:

in the case of a hydrophilic object, rendering the surface of an object to be measured hydrophobic by using a vapor of a solution which is hydrophobic to the surface of said object to be measured;

bringing a drop of said solution into contact with the surface of said object to be measured and holding said drop thereon, and moving said drop on the surface of said object to be measured by a combination of rotational and linear motions;

recovering said drop after the movement; and analyzing said recovered drop by chemical analysis to determine the type and content of an impurity adsorbed on the surface of said object to be measured.

* * * * *